United States Patent
Nishikawa et al.

(10) Patent No.: US 11,389,073 B2
(45) Date of Patent: *Jul. 19, 2022

(54) BAG-SHAPED STRUCTURE, CUFF FOR BLOOD PRESSURE MONITOR, AND BLOOD PRESSURE MONITOR

(71) Applicants: OMRON CORPORATION, Kyoto (JP); OMRON HEALTHCARE CO., LTD., Muko (JP)

(72) Inventors: Kazuyoshi Nishikawa, Ritto (JP); Shuhei Ojiro, Kyoto (JP); Tomoyuki Nishida, Takatsuki (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 344 days.

This patent is subject to a terminal disclaimer.

(21) Appl. No.: 16/468,395

(22) PCT Filed: Dec. 26, 2017

(86) PCT No.: PCT/JP2017/046651
§ 371 (c)(1),
(2) Date: Jun. 11, 2019

(87) PCT Pub. No.: WO2018/146967
PCT Pub. Date: Aug. 16, 2018

(65) Prior Publication Data
US 2021/0282658 A1    Sep. 16, 2021

(30) Foreign Application Priority Data
Feb. 7, 2017    (JP) .............................. JP2017-020530

(51) Int. Cl.
*A61B 5/02*    (2006.01)
*A61B 5/022*    (2006.01)
(Continued)

(52) U.S. Cl.
CPC .......... *A61B 5/02233* (2013.01); *A61B 5/681* (2013.01); *A61B 5/0235* (2013.01); *A61B 5/742* (2013.01); *A61B 2560/0214* (2013.01)

(58) Field of Classification Search
CPC ................ A61B 5/02233; A61B 5/681; A61B 2560/0214; A61B 5/742; A61B 5/0235; A61B 5/022
See application file for complete search history.

(56) References Cited

U.S. PATENT DOCUMENTS

| 3,760,795 A | 9/1973 | Adelhed |
| 4,637,394 A | 1/1987 | Racz et al. |

(Continued)

FOREIGN PATENT DOCUMENTS

| CN | 1308918 A | 8/2001 | |
| CN | 2595322 Y | * 12/2003 | ............ A61B 5/021 |

(Continued)

OTHER PUBLICATIONS

English-language machine translation of CN-2595322-Y (Year: 2021).*

(Continued)

*Primary Examiner* — Andrey Shostak
(74) *Attorney, Agent, or Firm* — Harness, Dickey & Pierce, P.L.C.

(57) ABSTRACT

A bag-shaped structure for a blood pressure monitor cuff that is wrapped around a living body and is inflated by supplying a fluid to an internal space to apply a pressure to the living body, includes an inner wall portion that is positioned on the living body's side, has a Shore A hardness of 15 to 75, and has a thickness of 0.10 mm to 0.40 mm, an outer wall portion that faces the inner wall portion, and a pair of side wall portions that are provided in a manner to be continuous with the inner wall portion and the outer wall portion, have a (Continued)

Shore A hardness equal to the Shore A hardness of the inner wall portion, and have a thickness that falls within a range of 0.15 mm to 0.60 mm and is equal to or greater than a thickness of the inner wall portion.

7 Claims, 4 Drawing Sheets

(51) Int. Cl.
*A61B 5/00* (2006.01)
*A61B 5/0235* (2006.01)

(56) References Cited

U.S. PATENT DOCUMENTS

| | | | |
|---|---|---|---|
| 6,514,212 B1* | 2/2003 | Ide | A61B 5/021 600/485 |
| 6,527,727 B2 | 3/2003 | Itonaga et al. | |
| 6,592,565 B2* | 7/2003 | Twardowski | A61M 25/00 604/175 |
| 6,758,821 B2 | 7/2004 | Itonaga et al. | |
| 6,866,636 B2 | 3/2005 | Inoue et al. | |
| 7,794,405 B2 | 9/2010 | Karo et al. | |
| 2001/0016692 A1* | 8/2001 | Itonaga | A61B 5/02233 600/499 |
| 2003/0055347 A1 | 3/2003 | Itonaga et al. | |
| 2004/0034308 A1 | 2/2004 | Inoue et al. | |
| 2006/0135873 A1 | 6/2006 | Karo et al. | |
| 2006/0178584 A1 | 8/2006 | Karo et al. | |
| 2006/0184054 A1* | 8/2006 | Sano | A61B 5/021 600/499 |
| 2010/0004676 A1 | 1/2010 | McEwen et al. | |
| 2012/0016248 A1 | 1/2012 | Pollyea | |
| 2014/0011172 A1* | 1/2014 | Lowe | G09B 23/281 434/273 |
| 2015/0088011 A1 | 3/2015 | Taniguchi et al. | |
| 2015/0105676 A1 | 4/2015 | Uesaka et al. | |
| 2018/0153418 A1 | 6/2018 | Sullivan et al. | |
| 2019/0261870 A1 | 8/2019 | Nishikawa | |
| 2020/0187799 A1 | 6/2020 | Nishikawa et al. | |

FOREIGN PATENT DOCUMENTS

| | | | | |
|---|---|---|---|---|
| CN | 1470217 | A | | 1/2004 |
| CN | 1792320 | A | | 6/2006 |
| CN | 1813626 | A | | 8/2006 |
| CN | 1820702 | A | | 8/2006 |
| CN | 104394761 | A | | 3/2015 |
| CN | 104811517 | A | | 7/2015 |
| JP | S56076933 | A | | 6/1981 |
| JP | S61-037135 | A | | 2/1986 |
| JP | H09117419 | A | | 5/1997 |
| JP | 2001-224558 | A | | 8/2001 |
| JP | 2002224056 | A * | 8/2002 | A61B 5/022 |
| JP | 2003144398 | A | | 5/2003 |
| JP | 2003325462 | A | | 11/2003 |
| JP | 2004016566 | A | | 1/2004 |
| JP | 2006174860 | A | | 7/2006 |
| JP | 2006-218178 | A | | 8/2006 |
| JP | 3168377 | U | | 6/2011 |
| JP | 2012075780 | A | | 4/2012 |
| JP | 2013031545 | A | | 2/2013 |
| WO | 2016205549 | A1 | | 12/2016 |
| WO | WO-2017/017991 | A1 | | 2/2017 |

OTHER PUBLICATIONS

English-language machine translation of JP-2002224056-A (Year: 2021).*
Office Action for Japanese Patent Application No. 2017-020530 dated Jun. 2, 2020 with English translation (6 pages).
International Preliminary Report on Patentability for International Application No. PCT/JP2017/046651, dated Aug. 13, 2019, (7 pages).
International Search Report (in English and Japanese) and Written Opinion (in Japanese) issued in PCT/JP2017/046651, dated Feb. 6, 2018; ISA/JP.
Chinese Office Action for Application No. 201780076337.2 dated May 14, 2021 with English translation (14 pages).
U.S. Appl. No. 16/468,361, filed Jun. 11, 2019, Kazuyoshi Nishikawa.
U.S. Appl. No. 16/349,034, filed May 10, 2019, Kazuyoshi Nishikawa.
U.S. Appl. No. 16/468,450, filed Jun. 11, 2019, Kazuyoshi Nishikawa.
Chinese Office Action dated Sep. 7, 2021 (with English translation) for Chinese Application No. 201780076346.1 (16 pages).
Chinese Office Action dated Oct. 9, 2021 (with English Translation) for Chinese Application No. 201780076304.8 (11 pages).
Chinese Office Action for Chinese Application No. 201780068495.3 (with English Translation) dated Nov. 18, 2021 (13 pages).
International Search Report (in English and Japanese) and Written Opinion (in English and Japanese) issued in PCT/JP2017/046646, dated Feb. 27, 2018; ISA/JP.
International Preliminary Report on Patentability for International Application No. PCT/JP2017/046646, dated Jul. 11, 2019, (7 pages).
Japanese Office Action dated Sep. 29, 2020 (with English translation) for Japanese Patent Application No. 2016-254274 (12 pages).
Japanese Office Action dated Mar. 30, 2021 for Japanese Patent Application No. 2016-254274 with English translation (5 pages).
First Chinese Office Action for corresponding Application No. 201780068495.3 dated Apr. 20, 2021 with English translation (17 Pages).
International Search Report (in English and Japanese) and Written Opinion (in Japanese) issued in PCT/JP2017/046648, dated Feb. 6, 2018; ISA/JP.
International Preliminary Report on Patentability for International Application No. PCT/JP2017/046648, dated Aug. 13, 2019, (6 pages).
Office Action regarding Chinese Patent Application No. 201780076346.1, dated May 21, 2021.
International Search Report (in English and Japanese) and Written Opinion (in Japanese) issued in PCT/JP2017/046653, dated Mar. 20, 2018; ISA/JP.
International Preliminary Report on Patentability for International Application No. PCT/JP2017/046653, dated Aug. 13, 2019.
Japanese Office Action dated Aug. 11, 2020 (with English translation) for Japanese Patent Application No. 2017-024244 (5 pages).
Chinese Office Action dated May 11, 2021 for Application No. 201780076304.8 with English translation (18 pages).

* cited by examiner

BAG-SHAPED STRUCTURE, CUFF FOR BLOOD PRESSURE MONITOR, AND BLOOD PRESSURE MONITOR

CROSS-REFERENCE TO RELATED APPLICATIONS

This is a U.S. National Phase Application under 35 U.S.C. 371 of International Application No. PCT/JP2017/046651 (not published in English), filed Dec. 26, 2017, which claims priority to Japanese Patent Application No. 2017-020530, filed Feb. 7, 2017. The disclosures of the above applications are incorporated herein by reference.

FIELD

The present invention relates to a bag-shaped structure, a cuff for a blood pressure monitor, and a blood pressure monitor.

BACKGROUND

In recent years, blood pressure monitors are used not only in medical facilities but also in households for the purpose of checking health conditions. A blood pressure monitor measures a blood pressure by a cuff including a bag-shaped structure being wrapped around an upper arm or a wrist, etc. of a human body and being inflated and deflated to detect a pulse sound generated in an artery and vibrations of an arterial wall. Such a blood pressure monitor is required to have a cuff reduced in width in order to improve handleability and achieve size reduction.

In a known cuff for use in a blood pressure monitor, a fluid bag as an inflatable bag-shaped structure is provided in a belt-like bag having an outer cuff piece and an inner cuff piece. A known fluid bag has an outer wall portion, an inner wall portion, a pair of side wall portions, and a coupling portion, in which the outer wall portion faces the outer cuff piece, the inner wall portion faces the inner cuff piece, the side wall portions are integrally joined to the outer wall portion and the inner wall portion and are folded inside the fluid bag, and the coupling portion couples the side wall portions together inside the fluid bag (see, for example, Jpn. Pat. Appln. KOKAI Publication No. 2001-224558).

The coupling portion that couples the side wall portions together inside the fluid bag enables the fluid bag to maintain its shape in which the side wall portions are folded. The side wall portions are coupled together by the coupling portion. Thus, when the fluid bag is inflated, outward inflation of these side wall portions is restricted and the cuff is inflated in the thickness direction. This enables the cuff to press a measurement site more stably and attain high compression performance.

SUMMARY OF THE INVENTION

A blood pressure monitor using the aforementioned bag-shaped structure in a cuff may achieve the excellent blood pressure measurement accuracy. However, the inventors of the present invention have found room for improvement in blood pressure measurement accuracy especially in the case where a cuff is reduced in width. Specifically, when a cuff is reduced in width with an existing material constitution, a blood-vessel pressing area is decreased to cause a variation in measured blood pressure values. This variation in blood pressure values occurs as an error SD (so-called standard deviation). Therefore, to realize stable blood-vessel pressing characteristics with a cuff reduced in width, it is necessary to improve the conformability to a living body and to reduce a pressing pressure loss due to inflation at sites other than a site that conforms to the living body.

It is an object of the present invention to provide a bag-shaped structure that can achieve high blood pressure measurement accuracy even with a cuff reduced in width.

According to a first aspect of the present invention, there is provided a bag-shaped structure for use in a cuff for a blood pressure monitor that is wrapped around a living body and is inflated by supplying a fluid to an internal space to apply a pressure to the living body, comprising an inner wall portion that is positioned on a living body's side, has a Shore A hardness within a range of 15 to 75, and has a thickness within a range of 0.10 mm to 0.40 mm, an outer wall portion that faces the inner wall portion, and a pair of side wall portions that are provided in a manner to be continuous with the inner wall portion and the outer wall portion, have a Shore A hardness equal to a Shore A hardness of the inner wall portion, and have a thickness that falls within a range of 0.15 mm to 0.60 mm and is equal to or greater than a thickness of the inner wall portion.

Here, the Shore A hardness is a durometer hardness obtained by a type A durometer hardness testing specified in JIS K6253-3: 2012 ("Rubber, vulcanized or thermoplastic—Determination of hardness—Part 3: Durometer method").

According to a second aspect of the present invention, there is provided the bag-shaped structure according to the first aspect, wherein each of the side wall portions forming the pair is bent or folded toward the internal space.

According to a third aspect of the present invention, there is provided the bag-shaped structure according to the first aspect, wherein each of the side wall portions forming the pair has a plurality of regions bent or folded toward the internal space.

According to a fourth aspect of the present invention, there is provided the bag-shaped structure according to any one of the first to third aspects, further comprising a coupling portion between the inner wall portion and the outer wall portion, wherein the coupling portion couples the pair of side wall portions together.

According to a fifth aspect of the present invention, there is provided the bag-shaped structure according to any one of the first to fourth aspects, having a width within a range of 20 mm to 45 mm.

According to a sixth aspect of the present invention, there is provided a cuff for a blood pressure monitor, comprising the bag-shaped structure according to any one of the first to fifth aspects.

According to a seventh aspect of the present invention, there is provided a blood pressure monitor comprising the cuff according to the sixth aspect.

According to the first aspect, the inner wall portion has a Shore A hardness within a range of 15 to 70 and a thickness within a range of 0.10 mm to 0.40 mm, and the side wall portions have a Shore A hardness equal to that of the inner wall portion and a thickness that falls within a range of 0.15 mm to 0.60 mm and is equal to or greater than that of the inner wall portion. Therefore, even in the case where the cuff is reduced in width, a pressing pressure loss can be prevented from occurring due to inflation at sites other than a site that conforms to the living body, while achieving the high conformability to a living body. Thus, a variation in measured blood pressure values, that is, an error SD can be reduced, so that the high blood pressure measurement accuracy can be achieved.

According to the second aspect, each of the side wall portions forming the pair is bent or folded toward the internal space. Thus, the bag-shaped structure is easily deformed in its thickness direction when it is inflated.

According to the third aspect, each of the side wall portions forming the pair has a plurality of regions bent toward the internal space. Thus, the bag-shaped structure is deformed more easily in its thickness direction when it is inflated.

According to the fourth aspect, the bag-shaped structure further includes a coupling portion between the inner wall portion and the outer wall portion, and this coupling portion couples the pair of side wall portions together. Thus, the bag-shaped structure is hardly deformed in its width direction when it is inflated.

According to the fifth aspect, the width falls within a range of 20 mm to 45 mm. Thus, the effect obtained by adopting the above configuration becomes most remarkable.

According to the sixth aspect, the bag-shaped structure according to any one of the first to fifth aspects is used in a cuff for a blood pressure monitor. Thus, the high blood pressure measurement accuracy can be achieved even with the cuff reduced in width.

According to the seventh aspect, the cuff according to the sixth aspect is used in a blood pressure monitor. Thus, the high blood pressure measurement accuracy can be achieved even with the cuff reduced in width.

DETAILED DESCRIPTION

Figure 1:
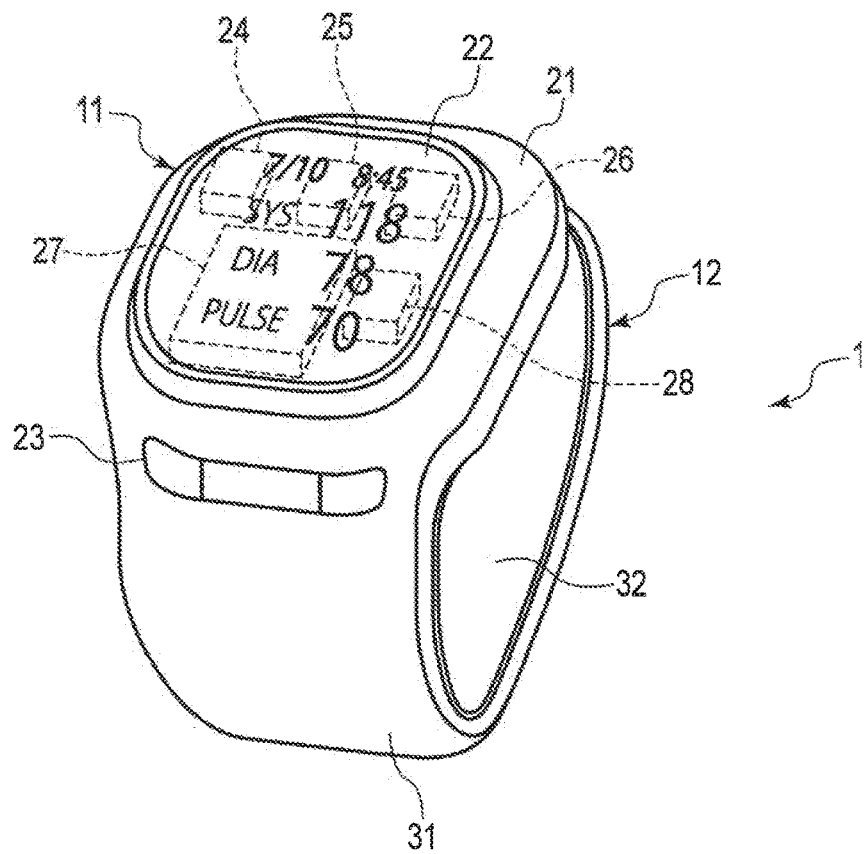
FIG. 1 is a perspective view schematically showing a blood pressure monitor according to an embodiment of the present invention.

Hereinafter, embodiments of the present invention will be described with reference to the drawings. Elements having the same or similar functions are denoted by the same reference numerals, and redundant explanations will be omitted.

<Blood Pressure Monitor>

Figure 2:
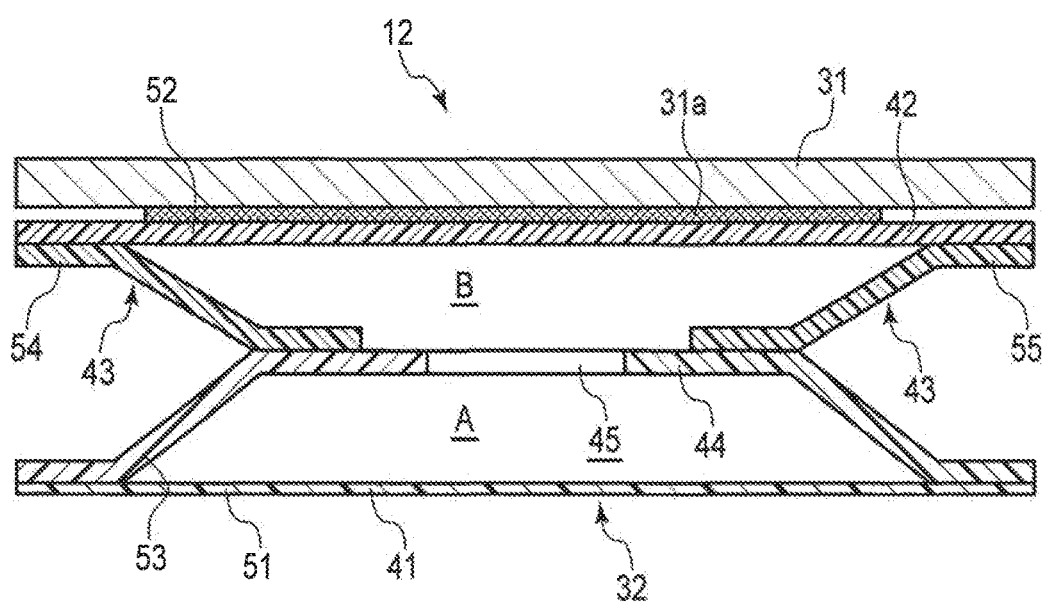
FIG. 2 is a cross-sectional view schematically showing a cuff included in the blood pressure monitor shown in FIG. 1.
Figure 3:
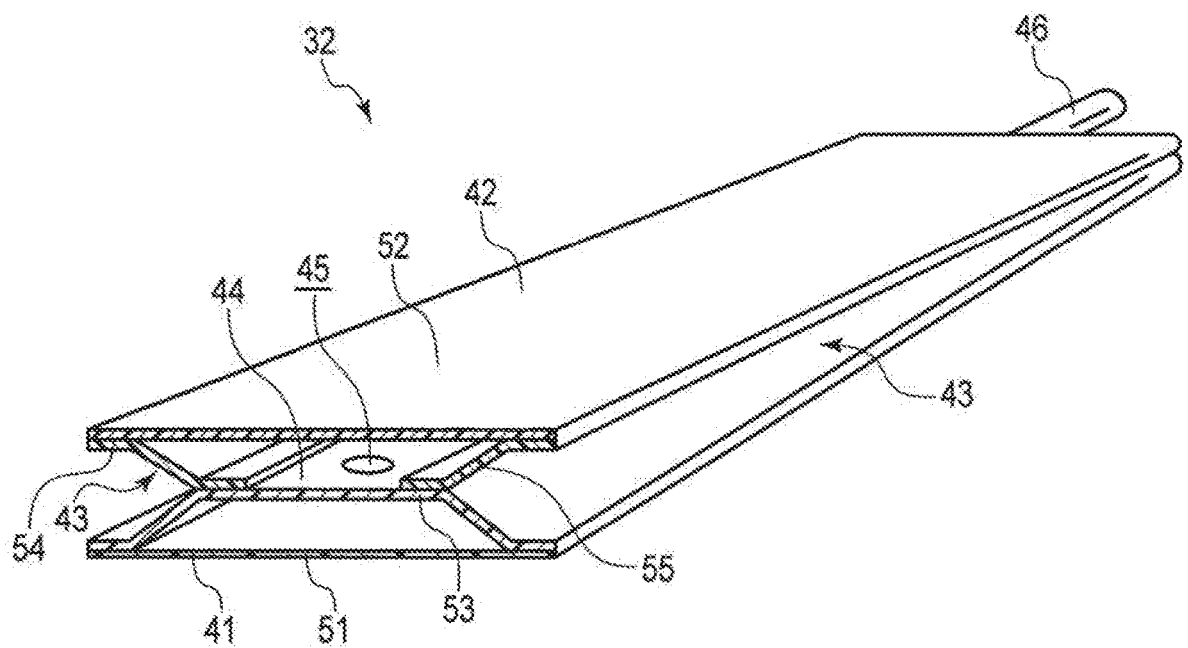
FIG. 3 is a broken perspective view schematically showing a bag-shaped structure included in the cuff shown in FIG. 2.
Figure 4:
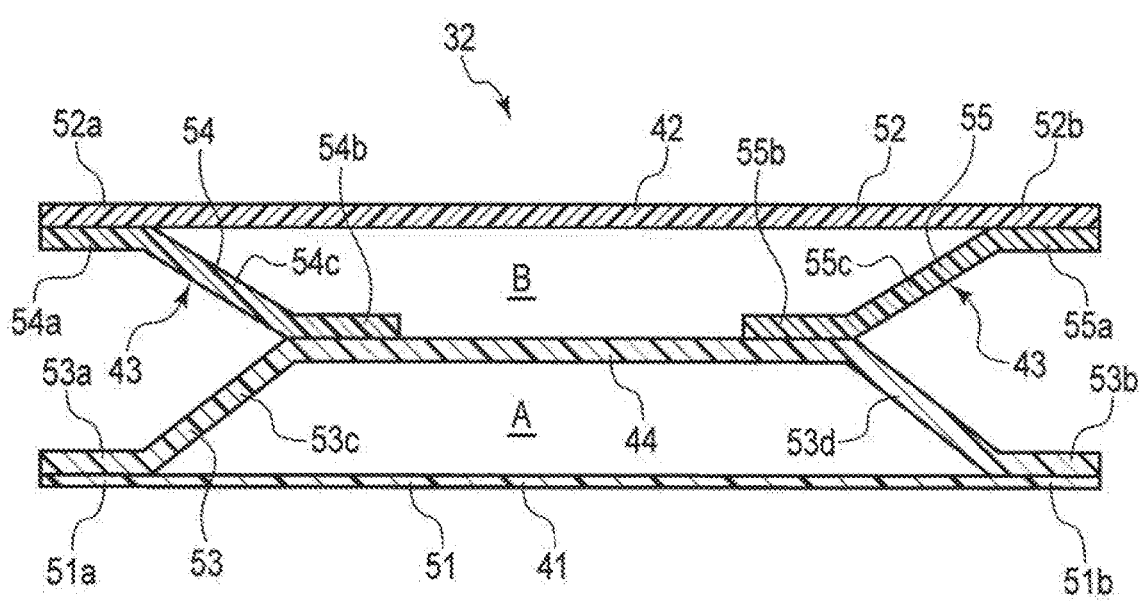
FIG. 4 is a cross-sectional view schematically showing the bag-shaped structure shown in FIG. 3.

FIG. 1 is a perspective view schematically showing a blood pressure monitor according to an embodiment of the present invention. FIG. 2 is a cross-sectional view schematically showing a cuff included in the blood pressure monitor shown in FIG. 1. FIG. 3 is a broken perspective view schematically showing a bag-shaped structure included in the cuff shown in FIG. 2. FIG. 4 is a cross-sectional view schematically showing the bag-shaped structure shown in FIG. 3.

The blood pressure monitor 1 shown in FIG. 1 is an electronic blood pressure monitor to be fitted on a living body, specifically, on a wrist. The blood pressure monitor 1 may be fitted on any of other sites of the living body.

The blood pressure monitor 1 includes an apparatus body 11 and a cuff 12.

The apparatus body 11 includes a case 21, a display unit 22, an operation unit 23, a flow path (not shown), a pump 24, a valve 25, a pressure sensor 26, a power supply unit 27, and a control unit 28.

The upper part of the case 21 includes openings for the display unit 22 and the operation unit 23. Here, the case 21 is a component that is integral with a base member 31 of the cuff 12 to be described later. The case 21 may be a component separate from the base member 31.

The display unit 22 is installed in the case 21 so as to display images at the position of the opening provided in the upper part of the case 21. The display unit 22 is, for example, a liquid crystal display or an organic electroluminescence display. The display 22 displays various information including measurements such as blood pressure values, e.g., a systolic blood pressure and a diastolic blood pressure, and a heart rate.

The operation unit 23 includes buttons for a user to, e.g., start/stop measurement, turn on/off the power supply, select functions, and make various settings. The operation unit 23 is installed in the case 21 so that those buttons are exposed to the external space of the case 21 at the position of the opening described above. The operation unit 23 outputs electric signals corresponding to commands or information input via the buttons. In the case where a touch-panel display is used as the display unit 22, this panel may be utilized as the operation unit.

The flow path is installed in the case 21. According to an example, the flow path has a structure branched in four directions and includes four openings. One of those openings is connected to an intake/exhaust port of the bag-shaped structure 32 included in the cuff 12.

The pump 24 is installed in the case 21. An exhaust port of the pump is connected to another one of the openings included in the flow path. The pump is, for example, a rolling pump. The pump discharges compressed air from its exhaust port.

The valve 25 is installed in the case 21. The valve 25 is connected to yet another one of the openings included in the flow path. The valve 25 is a valve whose operation is controllable using electric power, for example, a solenoid valve. The valve 25 opens and closes the opening to which the valve 25 is attached.

The pressure sensor 26 is installed in the case 21.

The pressure sensor 26 is connected to the remaining one of the openings included in the flow path. The pressure sensor 26 is, for example, a piezoresistive type pressure sensor. The pressure sensor 26 detects pressure within the flow path and outputs an electric signal corresponding to this pressure.

The power supply unit 27 is installed in the case 21. The power supply unit 27 contains a battery, for example, a lithium ion secondary battery. The power supply unit 27 is electrically connected to the control unit 28. The power supply unit 27 supplies electric power to the control unit 28.

The control unit 28 is installed in the case 21. The control unit 28 is electrically connected to the display unit 22, the operation unit 23, the pump 24, the valve 25, and the pressure sensor 26, and supplies electric power to them. Furthermore, the control unit 28 controls the operation of the display unit 22, the pump 24, and the valve 25 based on electric signals output from the operation unit 23 and the pressure sensor 26.

For example, when an electric signal corresponding to the start of measurement is supplied from the operation unit 23, the control unit 28 controls the operation of the valve 25 and the pump 24 in a manner such that the valve 25 is closed and then the pump 24 starts driving. The control unit 28 then determines a timing for stopping the operation of the pump 24, based on electric signals output from the pressure sensor 26, and controls the operation of the pump 24 and the valve 25 in a manner such that the pump 24 stops operating at the determined timing and then the valve 25 is gradually opened. Subsequently, the control unit 28 obtains a measurement result such as blood-pressure values of the highest and lowest blood pressures, and a heart rate, from electric signals output from the pressure sensor 26, and outputs video signals corresponding to the measurement result to the display unit 22.

The cuff 12 is formed integrally with the apparatus body 11. As shown in FIGS. 1 and 2, the cuff 12 includes the base member 31, a fastener (not shown), a joint layer 31a, and a bag-shaped structure 32.

The base member 31 is a belt-shaped member with low stretchability. The base member 31 is made of, for example, resin. The base member 31 supports the bag-shaped structure 32 and enables the cuff 12 to be wrapped around a living body. Furthermore, when the bag-shaped structure 32 is inflated, the base member 31 suppresses inflation toward the side opposite to a living body without hindering inflation toward the living body.

The base member 31 has one end integrated with the case 21 and the other end joined to the fastener, etc. As described above, the case 21 and the base member 31 may be separate components. To facilitate the fitting of the cuff 12 on a living body, the base member 31 may be formed into the shape curved along a shape of a site on which the cuff 12 is to be fitted.

The fastener enables the aforementioned other end of the base member 31 to be fixed to the case 21. The faster is, for example, a tri-fold buckle in which one end is supported by the aforementioned other end of the base member 31 and the other end is supported by the case 21.

The joint layer 31a is supported by one of the main surface of the base member 31 that faces a living body when the cuff 12 is fitted on the living body. The base member 31 and the bag-shaped structure 32 are joined together by the joint layer 31a. The joint layer 31a is, for example, an adhesion layer or a double-sided adhesive tape.

As shown in FIGS. 2 to 4, the bag-shaped structure 32 includes an inner wall portion 41, an outer wall portion 42, a pair of side wall portions 43, a coupling portion 44, and a connection tube 46.

The inner wall portion 41 and the outer wall portion 42 have a rectangular shape and face each other. The inner wall portion 41 and the outer wall portion 42 have the same longitudinal direction as that of the base member 31. As shown in FIG. 2, the outer wall portion 42 is joined to the base member 31 via the joint layer 31a.

As shown in FIGS. 2 to 4, the pair of side wall portions 43 are provided in a manner to be continuous with the inner wall portion 41 and the outer wall portion 42 between a pair of edge portions along the longitudinal direction of the inner wall portion 41 and the outer wall portion 42. An internal space of the bag-shaped structure 32 is defined by these inner wall portions 43 in conjunction with the inner wall portion 41 and the outer wall portion 42. The side wall portions 43 promote deformation of the bag-shaped structure 32 in a direction that the inner wall portion 41 and the outer wall portion 42 move away from each other, that is, deformation in the thickness direction of the bag-shaped structure 32 when a pressure in the internal space of the bag-shaped structure 32 is increased.

Each of the side wall portions 43 is shaped to be bent or folded toward the inside of the bag-shaped structure 32. This structure further promotes deformation of the bag-shaped structure 32 in its thickness direction when it is inflated. Each of the side wall portions 43 may not be shaped to be bent or folded toward the inside of the bag-shaped structure 32.

The coupling portion 44 is positioned between the inner wall portion 41 and the outer wall portion and couples the pair of side wall portions 43 together. The coupling portion 44 divides the internal space of the bag-shaped structure 32 into an internal space A and an internal space B. The internal space A is surrounded by the inner wall portion 41, the coupling portion 44, and the pair of side wall portions 43. The internal space B is surrounded by the outer wall portion 42, the coupling portion 44, and the pair of side wall portions 43. The coupling portion 44 is provided with one or more communication holes 45 that allow communication between the internal space A and the internal space B. The coupling portion 44 suppresses deformation of the bag-shaped structure 32 in its width direction when it is inflated. The coupling portion 44 can be omitted.

Here, the structure including the inner wall portion 41, the outer wall portion 42, the pair of side wall portions 43, and the coupling portion 44 is formed of five sheet members 51 to 55, as shown in FIGS. 2 to 4.

The sheet members 51 and 52 have a rectangular shape and face each other. The two edge portions along the width direction of the sheet member 51 are joined to the two edge portions along the width direction of the sheet member 52, respectively. The sheet members 51 and 52 form the inner wall portion 41 and the outer wall portion 42, respectively.

The sheet member 53 has a rectangular shape and is positioned between the sheet member 51 and the sheet member 52. As shown in FIG. 4, edge portions 53a and 53b along the longitudinal direction of the sheet member 53 are joined to edge portions 51a and 51b along the longitudinal direction of the sheet member 51, respectively. The two edge portions along the width direction of the sheet member 53 are joined to the two edge portions along the width direction of the sheet member 51, respectively. In the sheet member 53, a portion extending in the longitudinal direction between the edge portion 53a and the edge portion 53b forms the coupling portion 44. In the sheet member 53, the portion forming the coupling portion 44 is provided with the communication hole 45 shown in FIGS. 2 and 3. In the sheet member 53, furthermore, as shown in FIG. 4, a portion 53c between the edge portion 53a and the coupling portion 44 forms a part of one of the side wall portions 43, and a portion 53d between the edge portion 53b and the coupling portion 44 forms a part of the other side wall portion 43.

The sheet member 54 has a rectangular shape and is positioned between the sheet member 52 and the sheet member 53. One edge portion 54a along the longitudinal direction of the sheet member 54 is joined to one edge portion 52a along the longitudinal direction of the sheet member 52. The other edge portion 54b along the longitudinal direction of the sheet member 54 is joined to the sheet member 53 at a position adjacent to the portion 53c of the sheet 53 that forms a part of one of the side wall portions 43. The two edge portions along the width direction of the sheet member 54 are joined to the two edge portions along the width direction of the sheet member 52, respectively. A portion 54c of the sheet member 54 that is positioned between the edge portion 54a and the edge portion 54b forms the remaining parts of one of the side wall portions 43.

The sheet member 55 has a rectangular shape and is positioned between the sheet member 52 and the sheet member 53. One edge portion 55a along the longitudinal direction of the sheet member 55 is joined to the other edge portion 52b along the longitudinal direction of the sheet member 52. The other edge portion 55b along the longitudinal direction of the sheet member 55 is joined to the sheet member 53 at a position adjacent to the portion 53d of the sheet 53 that forms a part of the other side wall portion 43. The two edge portions along the width direction of the sheet member 55 are joined to the two edge portions along the width direction of the sheet member 52, respectively. In the sheet member 55, a portion 55c positioned between the edge portion 55a and the edge portion 55b forms the remaining parts of the other side wall portion 43.

Each of the sheet members that form the bag-shaped structure 32 is made of, for example, elastomer. Each of the sheet members may have a single-layer structure or a multilayer structure.

The elastomer is, for example, thermoset elastomer or thermoplastic elastomer.

As the thermoplastic elastomer, for example, thermoplastic polyurethane (hereinafter, referred to as "TPU" or "TPU resin"), hydrogenated styrene-based thermoplastic elastomer such as styrene-ethylene/butylene-styrene block copolymer (hereinafter, referred to as "SEBS"), polyvinyl chloride resin, ethylene-vinyl acetate resin, thermoplastic polystyrene resin, thermoplastic polyolefin resin, thermoplastic polyester resin, or thermoplastic polyamide resin can be used. As the thermoplastic elastomer, it is preferable to use TPU or SEBS.

As the thermoset elastomer, for example, urethane rubber, fluoro-rubber, or silicone resin can be used. As the thermoset elastomer, it is preferable to use silicone resin.

The sheet members that form the bag-shaped structure 32 are joined together by, for example, laser welding, high frequency welding, hot press welding, or an adhesive or a double-sided tape.

In the case where a pair of the sheet members to be joined together are made of thermoplastic elastomer, they are joined together by, for example, laser welding, high frequency welding, or hot press welding.

In the case where at least one of the sheet members to be jointed together is made of thermoset elastomer, they are joined together by, for example, an adhesive or a double-sided tape. As the adhesive, for example, a molecular adhesive can be used.

Each of the sheet members can be formed by existing methods such as die-cast molding, T-die extrusion molding, injection molding, etc. A sheet member made of thermoset elastomer can be molded by, for example, die-cast molding.

A sheet member made of thermoplastic elastomer can be molded by, for example, T-die extrusion molding or injection molding.

The inner wall portion 41 has a Shore A hardness in the range of 15 to 75. When the inner wall portion 41 has a Shore A hardness under 15, its rigidity becomes insufficient to press a living body uniformly. When the inner wall portion 41 has a Shore A hardness beyond 75, its conformability to a living body becomes too low to achieve excellent blood-vessel pressing characteristics. Herein, the blood-vessel pressing characteristics mean, for example, the characteristics that the bag-shaped structure 32 can press blood vessels with an appropriate pressure.

The Shore A hardness of the inner wall portion 41 can be adjusted, for example, by changing the type of elastomer to be used for a sheet member. Alternatively, the Shore A hardness of the inner wall portion 41 can be adjusted by changing the ratio of a soft segment content to a hard segment content in the elastomer, or by controlling intermolecular crosslinking.

In the case of using a thermoplastic elastomer in the inner wall portion 41, this inner wall portion 41 has a Shore A hardness preferably in the range of 50 to 75. As this thermoplastic elastomer, it is preferable to use TPU resin, for example. If the thermoplastic elastomer such as TPU resin has a small Shore A hardness, there is a risk that a plasticizer, etc., is eluted.

In the case of using a thermoset elastomer in the inner wall portion 41, this inner wall portion 41 has a Shore A hardness preferably in the range of 15 to 50. As this thermoset elastomer, it is preferable to use silicone resin, for example.

Alternatively, in the case of using a thermoset elastomer such as silicone resin in the inner wall portion 41, the inner wall portion 41 has a Shore A hardness of preferably greater than 15 and less than 75, more preferably in the range of 20 to 60, and even more preferably in the range of 20 to 30. In this case, particularly high blood pressure measurement accuracy can be achieved if a Shore A hardness of the side wall portions 43 is set to be equal to that of the inner wall portion 41, and each of a thickness of the inner wall portion 41 and a thickness of the side wall portions 43 is set within an appropriate range.

The outer wall portion 42 is equal in Shore A hardness to, for example, the side wall portions 43. The outer wall portion 42 may be different in Shore A hardness from the side wall portions 43. In this case, the outer wall portion 42 may be larger or smaller in Shore A hardness than the side wall portions 43. In any case, as long as the side wall portions 43 are larger in Shore A hardness (higher in rigidity) than the inner wall portion 41, a loss in inflation pressure due to inflation of the side wall portions 43 is hardly caused when the bag-shaped structure 32 is inflated. This improves the inner wall portion 41 in characteristics of pressing a living body, so that excellent blood-vessel pressing characteristics can be achieved even in the case where a cuff is reduced in width.

A back plate may be installed between the outer wall portion 42 and the base member 31. With the back plate being installed, higher blood-vessel pressing characteristics can be achieved as in the case where the outer wall portion 42 is increased in Shore A hardness.

The side wall portions 43 are equal in Shore A hardness to the inner wall portion 41. If the side wall portions 43 and the inner wall portions are made different in Shore A hardness, such a difference in Shore A hardness affects a difference in moment of inertia area, thereby making it difficult to control blood-vessel pressing characteristics by adjusting a thickness of the inner wall portion 41 and a thickness of the side wall portions 43.

In the case of using a thermoplastic elastomer in the side wall portions 43, for example, TPU resin can be used as this thermoplastic elastomer. In the case of using a thermoset elastomer in the side wall portions 43, for example, silicone resin can be used as this thermoset elastomer.

In this bag-shaped structure 32, each of the side wall portions 43 has a thickness equal to or greater than that of the inner wall portion 41. If each of the side wall portions 43 is smaller in thickness than the inner wall portion 41, they are prone to cause abnormal inflation when the bag-shaped structure 32 is inflated, thereby not achieving high blood-vessel pressing characteristics.

In this bag-shaped structure 32, the inner wall portion 41 has a thickness within a range of 0.10 mm to 0.40 mm, while the side wall portions 43 have a thickness within a range of 0.15 mm to 0.60 mm. If the inner wall portion 41 is too thin, its rigidity becomes insufficient.

Thus, a site on which the cuff 12 is fitted cannot be uniformly pressed when the bag-shaped structure 32 is inflated. If the inner wall portion 41 is too thick, its conformability to a site on which the cuff 12 is fitted becomes insufficient when the bag-shaped structure 32 is inflated. Thus, high blood-vessel pressing characteristics cannot be achieved.

Preferably, the inner wall portion 41 has a thickness of greater than 0.10 mm and less than 0.20 mm, and each of the side wall portions 43 has a thickness of 0.15 mm or more and less than 0.40 mm. More preferably, the inner wall portion 41 has a thickness within a range of 0.12 mm to 0.18 mm, and each of the side wall portions 43 has a thickness within a range of 0.15 mm to 0.30 mm. In this case, particularly high blood pressure measurement accuracy can be achieved if a Shore A hardness of the inner wall portion 41 and the side wall portions 43 is set within an appropriate range.

Alternatively, the inner wall portion 41 has a thickness of 0.10 mm or more and less than 0.20 mm and each of the side wall portions 43 has a thickness of greater than 0.15 mm and less than 0.40 mm. More preferably, the inner wall portion 41 has a thickness within a range of 0.10 mm to 0.15 mm, and each of the side wall portions 43 has a thickness within a range of 0.25 mm to 0.35 mm. In this case also, particularly high blood pressure measurement accuracy can be achieved if a Shore A hardness of the inner wall portion 41 and the side wall portions 43 is set within an appropriate range.

One of the side wall portions 43 and the other side wall portion 43 may be the same or different in Shore A hardness. The latter configuration is effective in the case where, for example, the cuff is wrapped around a site having a tapered shape.

The outer wall portion 42 is equal in thickness to, for example, the side wall portions 43. The outer wall portion 42 may be different in thickness from the side wall portions 43. In this case, the outer wall portions 42 are preferably larger in thickness than the side wall portion 43. If the outer wall portion 42 is larger in thickness than the side wall portions 43, deformation is easily caused especially in the inner wall portion 41 when the bag-shaped structure 32 is inflated. Thus, even higher blood-vessel pressing characteristics can be achieved.

As shown in FIG. 3, the connection tube 46 fluidically connects the internal space defined by the inner wall portion 41, the outer wall portion 42, and the pair of side wall portions 43 to the flow path of the apparatus body 11.

The connection tube 46 is made of, e.g., resin, and has flexibility. One of the ends of the connection tube 46 is fixed between the edge portions along the width direction of the sheet members 51 and 52. The other end of the connection tube 46 is connected to the flow path of the apparatus body 11.

This bag-shaped structure 32 has a width preferably in the range of 20 mm to 45 mm, and more preferably in the range of 22 mm to 37 mm. If this width is too small, it is difficult to attain high blood-vessel pressing characteristics. If this width is large, the effect obtained by adopting the above configuration becomes most remarkable.

A distance from each of the edge portions 53a, 53b, 54a, and 55a to the coupling portion 44 is preferably in the range of 1 mm to 5 mm. If this distance is too short, deformation in the thickness direction of the bag-shaped structure 32 in association with its inflation becomes small. If this distance is too long, deformation in the thickness direction of the bag-shaped structure 32 in association with its inflation hardly occurs.

<Measurement of Blood Pressure Value>

Next, the measurement of blood pressure values using the blood pressure monitor 1 will be described with reference to FIGS. 1, 5, and 6.

Figure 5:
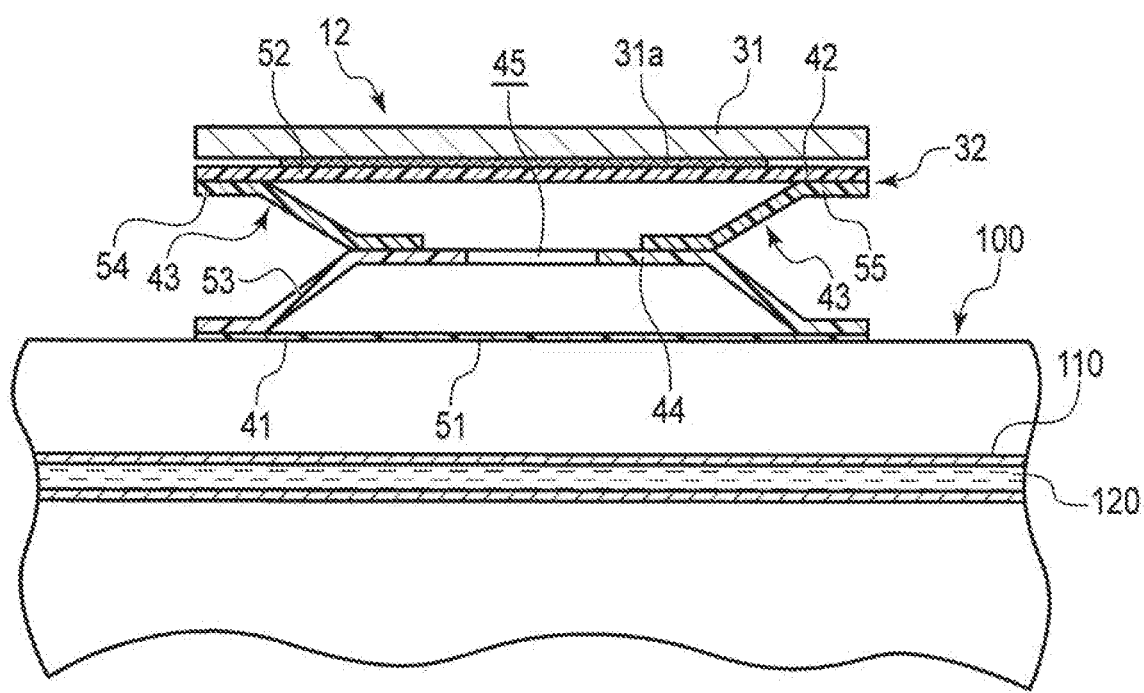
FIG. 5 is a cross-sectional view schematically showing a state in which the cuff shown in FIG. 2 is wrapped around a living body.
Figure 6:
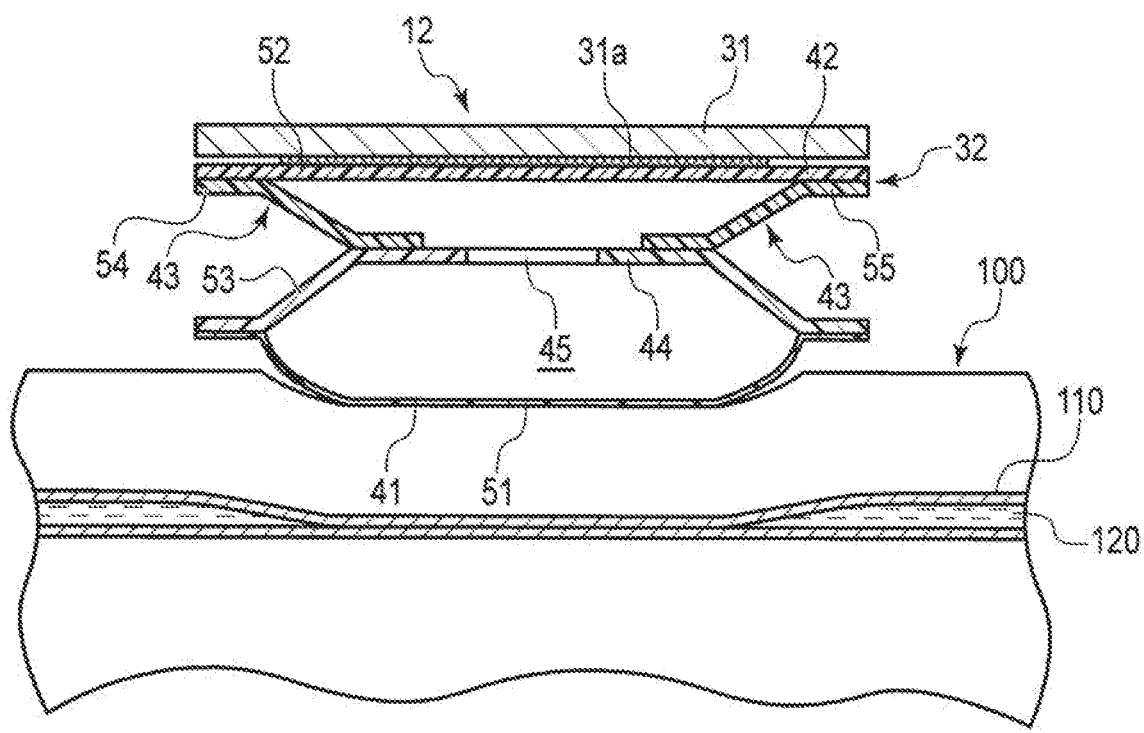
FIG. 6 is a cross-sectional view schematically showing a state in which the cuff shown in FIG. 2 is wrapped around a living body and the bag-shaped structure is inflated.

FIG. 5 is a cross-sectional view schematically showing a state in which the cuff shown in FIG. 2 is wrapped around a living body. FIG. 6 is a cross-sectional view schematically showing a state in which the cuff shown in FIG. 2 is wrapped around a living body and the bag-shaped structure is inflated. In the following description, a person to be measured is a user of the blood pressure monitor 1 shown in FIG. 1 and performs all operations relating to the measurement of blood pressure values by himself or herself.

To measure a blood pressure value, first, a person to be measured wears the cuff 12 on the wrist 100 as shown in FIG. 5. Next, the person to be measured operates the operation unit 23 shown in FIG. 1 to input a command corresponding to the start of measurement of a blood pressure value.

When this command is input, the operation unit 23 outputs an electric signal corresponding to the start of measurement to the control unit 28. The control unit 28 supplied with this signal controls the operation of the valve 25 and the pump 24 in a manner such that the valve 25 is closed and the pump 24 starts driving. In this manner, the bag-shaped structure 32 starts inflating.

The pressure sensor 26 detects a pressure in the internal space of the bag-shaped structure 32 and outputs an electric signal corresponding to this pressure to the control unit 28. Based on this electrical signal, the control unit 28 determines whether or not the pressure in the internal space of the bag-shaped structure 32 has reached a predetermined level for blood pressure measurement. The control unit 28 then controls the operation of the pump 24 in a manner such that the pump 24 halts driving when this pressure has reached the aforementioned level. Immediately after the pump 24 halts driving, as shown in FIG. 6, the bag-shaped structure 32 is sufficiently inflated, and the cuff 12 occludes an artery 110 at the position of the wrist 100.

Thereafter, the control unit 28 controls the operation of the valve 25 in a manner such that the valve 25 is gradually opened. When the valve 25 is opened, the air inside the bag-shaped structure 32 is exhausted, thereby lowering the pressure in the internal space. In this decompression process, the flow of blood 120 in the artery 110 is resumed. From electric signals output from the pressure sensor 26 in this process, the control unit 28 obtains a measurement result such as blood-pressure values of, e.g., the highest and lowest blood pressures, a heart rate, etc., and outputs video signals corresponding to the measurement result to the display unit 22 shown in FIG. 1.

When the aforementioned video signals are supplied, the display unit 22 displays on its screen the measurement result such as blood-pressure values of, e.g., the highest and lowest blood pressures, a heart rate, etc. In this way, the measurement is terminated.

<Effect>

The above blood pressure monitor 1 can uniformly apply strong pressure over a wide range of a living body without causing abnormal inflation when the cuff 12 is fitted on the living body and the bag-shaped structure 32 is inflated. Therefore, even in the case where the cuff 12 is reduced in width, a pressing pressure loss due to inflation at portions other than the portion that conforms to the living body can be prevented from occurring, while achieving the high conformability to the living body.

Therefore, even with the cuff 12 reduced in width, a variation in measured blood pressure values, that is, an error SD can be reduced, so that the high blood pressure measurement accuracy can be achieved.

<Modifications of Bag-Shaped Structure>

The bag-shaped structure 32 described above can be modified in various ways.

[First Modification]

Figure 7:
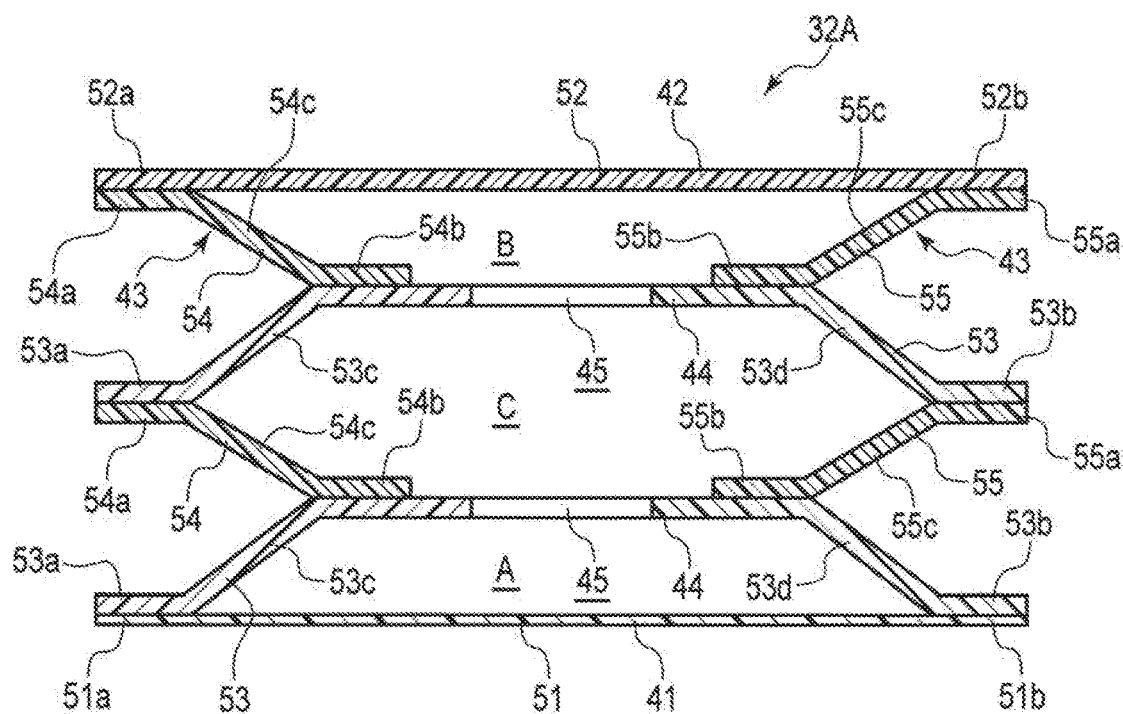
FIG. 7 is a cross-sectional view schematically showing a bag-shaped structure according to a first modification.

FIG. 7 is a cross-sectional view schematically showing a bag-shaped structure according to a first modification.

The bag-shaped structure 32A shown in FIG. 7 is the same as the bag-shaped structure 32 described with reference to FIGS. 2 to 4 except that the configuration described below is adopted. That is, in this bag-shaped structure 32A, each of the sheet members 53 to 55 is increased from 1 to 2 in number, and an internal space C surrounded by the pair of side wall portions 43 and the pair of coupling portions 44 is provided between the internal space A and the internal space B.

In this bag-shaped structure 32A, each of the side wall portions 43 forming the pair has a plurality of regions bent or folded toward the internal space. As compared to the bag-shaped structure 32 described with reference to FIGS. 2 to 4, this bag-shaped structure 32A is deformed more easily in its thickness direction when it is inflated. Therefore, even if the cuff is reduced in width, when this bag-shaped structure 32A is used in the cuff 12, the high blood pressure measurement accuracy can be achieved. Each of the side wall portions 43 forming the pair may have three or more regions bent or folded toward the internal space.

[Second Modification]

Figure 8:
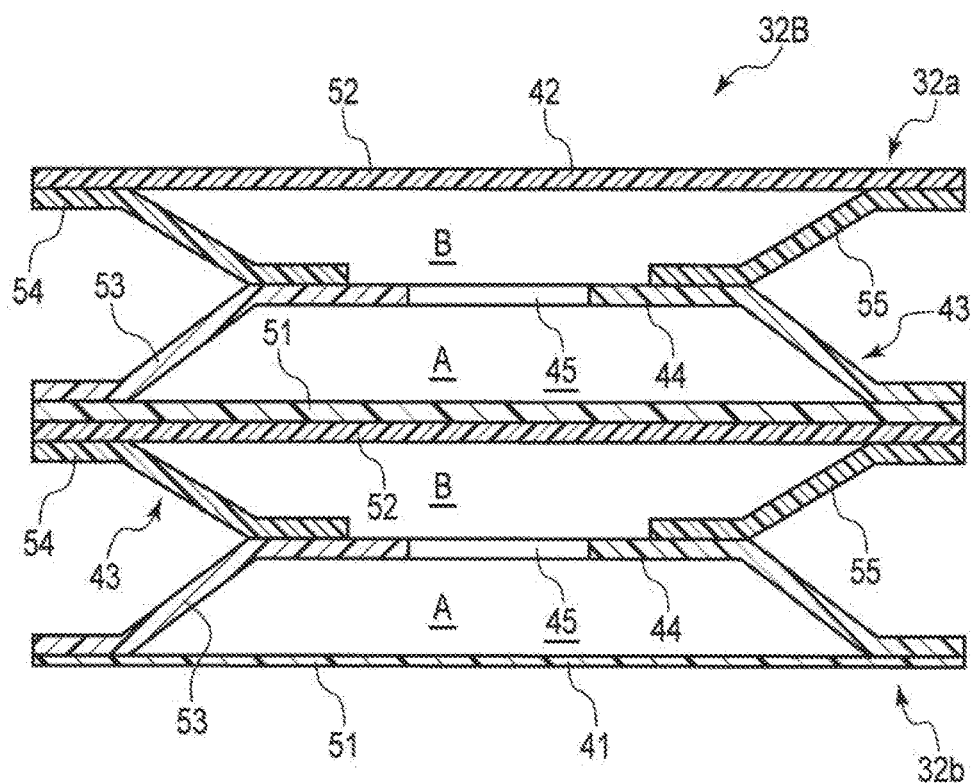
FIG. 8 is a cross-sectional view schematically showing a bag-shaped structure according to a second modification

FIG. 8 is a cross-sectional view schematically showing a bag-shaped structure according to a second modification.

The bag-shaped structure 32B shown in FIG. 8 is the same as the bag-shaped structure 32 described with reference to FIGS. 2 to 4 except that the configuration described below is adopted. That is, this bag-shaped structure 32B contains bag-shaped structures 32a and 32b each of which has the same configuration as that of the bag-shaped structure 32 described with reference to FIGS. 2 to 4. The bag-shaped structures 32a and 32b are stacked together in their thickness direction, and the sheet member 51 of the bag-shaped structure 32a is joined to the sheet member 52 of the bag-shaped structure 32b by an adhesive, for example. Each of the bag-shaped structures 32a and 32b includes the connection tube 46 described with reference to FIG. 3. These connection tubes 46 are connected to the flow path of the apparatus body 11 shown in FIG. 1.

In this bag-shaped structure 32B, one of the bag-shaped structures 32a and 32b can be used for the purpose of, for example, pressing a living body. The other of the bag-shaped structures 32a and 32b can be used for, for example, the sensing purpose, that is, for sensing a pulse wave as a vibration caused in a blood vessel wall.

Even if the cuff is reduced in width, when this bag-shaped structure 32B is used in the cuff 12, the high blood pressure measurement accuracy can be achieved.

The present invention is not limited to the above-described embodiments and can be modified in various manners in practice without departing from the gist of the invention. Moreover, the embodiments can be suitably combined where possible; in that case, combined advantages are obtained. Furthermore, the above-described embodiments include various stages of the invention, and various inventions can be extracted by suitably combining the structural elements disclosed herein. For example, if the object of the invention is achieved and the advantages of the invention are attained even after some of the structural elements are deleted from all the structural elements disclosed in the embodiments, the structure made up of the resultant structural elements can be extracted as an invention.

EXAMPLES

Specific examples of the present invention are described below.

<Manufacture of Bag-Shaped Structure>

Example 1

The bag-shaped structure 32 described with reference to FIGS. 2 to 4 was manufactured. In this example, as the sheet members 51 to 55, a sheet made of silicone resin with a Shore A hardness of 25 was used. The sheet member 51 had a thickness of 0.10 mm, and the sheet members 52 to 55 had a thickness of 0.15 mm. Furthermore, the bag-shaped structure 32 had a width of 27 mm. A distance from each of the edge portions 53a, 53b, 54a, and 55a to the coupling portion 44 was set to 3 mm. The sheet members had a joint width of 2 mm. The sheet members were jointed together using an adhesive.

Example 2

The bag-shaped structure was manufactured by the same method as in Example 1 except that the thickness of the sheet members 52 to 55 was changed from 0.15 mm to 0.30 mm.

Example 3

The bag-shaped structure was manufactured by the same method as in Example 1 except that the thickness of the sheet members 52 to 55 was changed from 0.15 mm to 0.40 mm.

Example 4

The bag-shaped structure was manufactured by the same method as in Example 1 except that the thickness of the sheet members 52 to 55 was changed from 0.15 mm to 0.60 mm.

Example 5

The bag-shaped structure was manufactured by the same method as in Example 1 except that the thickness of the sheet member 51 was changed from 0.10 mm to 0.15 mm.

Example 6

The bag-shaped structure was manufactured by the same method as in Example 1 except that the thickness of the sheet member 51 was changed from 0.10 mm to 0.15 mm and the thickness of the sheet members 52 to 55 was changed from 0.15 mm to 0.30 mm.

Example 7

The bag-shaped structure was manufactured by the same method as in Example 1 except that the thickness of the sheet member 51 was changed from 0.10 mm to 0.15 mm and the thickness of the sheet members 52 to 55 was changed from 0.15 mm to 0.40 mm.

Example 8

The bag-shaped structure was manufactured by the same method as in Example 1 except that the thickness of the sheet member 51 was changed from 0.10 mm to 0.15 mm and the thickness of the sheet members 52 to 55 was changed from 0.15 mm to 0.60 mm.

Example 9

The bag-shaped structure was manufactured by the same method as in Example 1 except that the thickness of the sheet member 51 was changed from 0.10 mm to 0.20 mm and the thickness of the sheet members 52 to 55 was changed from 0.15 mm to 0.30 mm.

Example 10

The bag-shaped structure was manufactured by the same method as in Example 1 except that the thickness of the sheet member 51 was changed from 0.10 mm to 0.20 mm and the thickness of the sheet members 52 to 55 was changed from 0.15 mm to 0.40 mm.

Example 11

The bag-shaped structure was manufactured by the same method as in Example 1 except that the thickness of the sheet member 51 was changed from 0.10 mm to 0.20 mm and the thickness of the sheet members 52 to 55 was changed from 0.15 mm to 0.60 mm.

Example 12

The bag-shaped structure was manufactured by the same method as in Example 1 except that the thickness of the sheet member 51 was changed from 0.10 mm to 0.40 mm and the thickness of the sheet members 52 to 55 was changed from 0.15 mm to 0.40 mm.

Example 13

The bag-shaped structure was manufactured by the same method as in Example 1 except that the thickness of the sheet member 51 was changed from 0.10 mm to 0.40 mm and the thickness of the sheet members 52 to 55 was changed from 0.15 mm to 0.60 mm.

Example 14

The bag-shaped structure was manufactured by the same method as in Example 1 except for the following. Namely, as the sheet members 51 to 55, a sheet made of silicone resin with a Shore A hardness of 15 was used instead of the sheet made of silicone resin with a Shore A hardness of 25. In addition, the thickness of the sheet member 51 was changed from 0.10 mm to 0.15 mm, and the thickness of the sheet members 52 to 55 was changed from 0.15 mm to 0.30 mm.

Example 15

The bag-shaped structure was manufactured by the same method as in Example 1 except for the following. Namely, as the sheet members 51 to 55, a sheet made of silicone resin with a Shore A hardness of 75 was used instead of the sheet made of silicone resin with a Shore A hardness of 25. In addition, the thickness of the sheet member 51 was changed from 0.10 mm to 0.15 mm, and the thickness of the sheet members 52 to 55 was changed from 0.15 mm to 0.30 mm.

Example 16

The bag-shaped structure was manufactured by the same method as in Example 1 except for the following. Namely, as the sheet members 51 to 55, a sheet made of silicone resin with a Shore A hardness of 15 was used instead of the sheet made of silicone resin with a Shore A hardness of 25. In addition, the thickness of the sheet member 51 was changed from 0.10 mm to 0.20 mm, and the thickness of the sheet members 52 to 55 was changed from 0.15 mm to 0.40 mm.

Example 17

The bag-shaped structure was manufactured by the same method as in Example 1 except for the following. Namely, as the sheet members 51 to 55, a sheet made of silicone resin with a Shore A hardness of 75 was used instead of the sheet made of silicone resin with a Shore A hardness of 25. In addition, the thickness of the sheet member 51 was changed from 0.10 mm to 0.20 mm, and the thickness of the sheet members 52 to 55 was changed from 0.15 mm to 0.40 mm.

Example 18

The bag-shaped structure was manufactured by the same method as in Example 1 except for the following. Namely, as the sheet members 51 to 55, a sheet made of TPU resin with a Shore A hardness of 75 was used instead of the sheet made of silicone resin with a Shore A hardness of 25. The joint width of the sheet members was changed from 2 mm to 1 mm. The sheet members were jointed together by high frequency welding instead of using the adhesive.

Example 19

The bag-shaped structure was manufactured by the same method as in Example 18 except that the thickness of the sheet members 52 to 55 was changed from 0.15 mm to 0.30 mm.

Example 20

The bag-shaped structure was manufactured by the same method as in Example 18 except that the thickness of the sheet members 52 to 55 was changed from 0.15 mm to 0.60 mm.

Example 21

The bag-shaped structure was manufactured by the same method as in Example 18 except that the thickness of the sheet member 51 was changed from 0.10 mm to 0.15 mm.

Example 22

The bag-shaped structure was manufactured by the same method as in Example 18 except that the thickness of the sheet member 51 was changed from 0.10 mm to 0.15 mm, and the thickness of the sheet members 52 to 55 was changed from 0.15 mm to 0.30 mm.

Example 23

The bag-shaped structure was manufactured by the same method as in Example 18 except that the thickness of the sheet member 51 was changed from 0.10 mm to 0.15 mm, and the thickness of the sheet members 52 to 55 was changed from 0.15 mm to 0.60 mm.

Example 24

The bag-shaped structure was manufactured by the same method as in Example 18 except that the thickness of the sheet member 51 was changed from 0.10 mm to 0.40 mm, and the thickness of the sheet members 52 to 55 was changed from 0.15 mm to 0.40 mm.

Example 25

The bag-shaped structure was manufactured by the same method as in Example 18 except that the thickness of the sheet member 51 was changed from 0.10 mm to 0.40 mm, and the thickness of the sheet members 52 to 55 was changed from 0.15 mm to 0.60 mm.

Comparative Example 1

The bag-shaped structure was manufactured by the same method as in Example 1 except that the thickness of the sheet members 52 to 55 was changed from 0.15 mm to 0.13 mm.

Comparative Example 2

The bag-shaped structure was manufactured by the same method as in Example 1 except that the thickness of the sheet members 52 to 55 was changed from 0.15 mm to 0.75 mm.

Comparative Example 3

The bag-shaped structure was manufactured by the same method as in Example 1 except that the thickness of the sheet member 51 was changed from 0.10 mm to 0.15 mm and the thickness of the sheet members 52 to 55 was changed from 0.15 mm to 0.13 mm.

Comparative Example 4

The bag-shaped structure was manufactured by the same method as in Example 1 except that the thickness of the sheet member 51 was changed from 0.10 mm to 0.15 mm and the thickness of the sheet members 52 to 55 was changed from 0.15 mm to 0.75 mm.

Comparative Example 5

The bag-shaped structure was manufactured by the same method as in Example 1 except that the thickness of the sheet member 51 was changed from 0.10 mm to 0.20 mm and the thickness of the sheet members 52 to 55 was changed from 0.15 mm to 0.13 mm.

Comparative Example 6

The bag-shaped structure was manufactured by the same method as in Example 1 except that the thickness of the sheet member 51 was changed from 0.10 mm to 0.20 mm.

Comparative Example 7

The bag-shaped structure was manufactured by the same method as in Example 1 except that the thickness of the sheet member 51 was changed from 0.10 mm to 0.20 mm and the thickness of the sheet members 52 to 55 was changed from 0.15 mm to 0.75 mm.

Comparative Example 8

The bag-shaped structure was manufactured by the same method as in Example 1 except that the thickness of the sheet member 51 was changed from 0.10 mm to 0.40 mm and the thickness of the sheet members 52 to 55 was changed from 0.15 mm to 0.13 mm.

Comparative Example 9

The bag-shaped structure was manufactured by the same method as in Example 1 except that the thickness of the sheet member 51 was changed from 0.10 mm to 0.40 mm.

Comparative Example 10

The bag-shaped structure was manufactured by the same method as in Example 1 except that the thickness of the sheet member 51 was changed from 0.10 mm to 0.40 mm and the thickness of the sheet members 52 to 55 was changed from 0.15 mm to 0.30 mm.

Comparative Example 11

The bag-shaped structure was manufactured by the same method as in Example 1 except that the thickness of the sheet member 51 was changed from 0.10 mm to 0.40 mm and the thickness of the sheet members 52 to 55 was changed from 0.15 mm to 0.75 mm.

Comparative Example 12

The bag-shaped structure was manufactured by the same method as in Example 1 except that the thickness of the sheet member 51 was changed from 0.10 mm to 0.05 mm.

Comparative Example 13

The bag-shaped structure was manufactured by the same method as in Example 1 except that the thickness of the sheet member 51 was changed from 0.10 mm to 0.50 mm.

Comparative Example 14

The bag-shaped structure was manufactured by the same method as in Example 1 except that the thickness of the sheet member 51 was changed from 0.10 mm to 0.05 mm and the thickness of the sheet members 52 to 55 was changed from 0.15 mm to 0.30 mm.

Comparative Example 15

The bag-shaped structure was manufactured by the same method as in Example 1 except that the thickness of the sheet member 51 was changed from 0.10 mm to 0.50 mm and the thickness of the sheet members 52 to 55 was changed from 0.15 mm to 0.30 mm.

Comparative Example 16

The bag-shaped structure was manufactured by the same method as in Example 1 except that the thickness of the sheet member 51 was changed from 0.10 mm to 0.05 mm and the thickness of the sheet members 52 to 55 was changed from 0.15 mm to 0.40 mm.

Comparative Example 17

The bag-shaped structure was manufactured by the same method as in Example 1 except that the thickness of the sheet member 51 was changed from 0.10 mm to 0.50 mm and the thickness of the sheet members 52 to 55 was changed from 0.15 mm to 0.40 mm.

Comparative Example 18

The bag-shaped structure was manufactured by the same method as in Example 1 except that the thickness of the sheet member 51 was changed from 0.10 mm to 0.05 mm and the thickness of the sheet members 52 to 55 was changed from 0.15 mm to 0.60 mm.

Comparative Example 19

The bag-shaped structure was manufactured by the same method as in Example 1 except that the thickness of the sheet member 51 was changed from 0.10 mm to 0.50 mm and the thickness of the sheet members 52 to 55 was changed from 0.15 mm to 0.60 mm.

Comparative Example 20

The bag-shaped structure was manufactured by the same method as in Example 1 except for the following. Namely, as the sheet members 51 to 55, a sheet made of silicone resin with a Shore A hardness of 10 was used instead of the sheet made of silicone resin with a Shore A hardness of 25. In addition, the thickness of the sheet member 51 was changed from 0.10 mm to 0.15 mm, and the thickness of the sheet members 52 to 55 was changed from 0.15 mm to 0.30 mm.

Comparative Example 21

The bag-shaped structure was manufactured by the same method as in Example 1 except for the following. Namely, as the sheet members 51 to 55, a sheet made of silicone resin with a Shore A hardness of 90 was used instead of the sheet made of silicone resin with a Shore A hardness of 25. In addition, the thickness of the sheet member 51 was changed from 0.10 mm to 0.15 mm, and the thickness of the sheet members 52 to 55 was changed from 0.15 mm to 0.30 mm.

Comparative Example 22

The bag-shaped structure was manufactured by the same method as in Example 1 except for the following. Namely, as the sheet members 51 to 55, a sheet made of silicone resin with a Shore A hardness of 10 was used instead of the sheet made of silicone resin with a Shore A hardness of 25. In addition, the thickness of the sheet member 51 was changed from 0.10 mm to 0.20 mm, and the thickness of the sheet members 52 to 55 was changed from 0.15 mm to 0.40 mm.

Comparative Example 23

The bag-shaped structure was manufactured by the same method as in Example 1 except for the following. Namely, as the sheet members 51 to 55, a sheet made of silicone resin with a Shore A hardness of 75 was used instead of the sheet made of silicone resin with a Shore A hardness of 25. In addition, the thickness of the sheet member 51 was changed from 0.10 mm to 0.20 mm, and the thickness of the sheet members 52 to 55 was changed from 0.15 mm to 0.40 mm.

Comparative Example 24

The bag-shaped structure was manufactured by the same method as in Example 1 except for the following. Namely, as the sheet members 51 to 55, a sheet made of TPU resin with a Shore A hardness of 75 was used instead of the sheet made of silicone resin with a Shore A hardness of 25. The thickness of the sheet members 52 to 55 was changed from 0.15 mm to 0.13 mm. The joint width of the sheet members was changed from 2 mm to 1 mm. The sheet members are jointed together by high frequency welding instead of using the adhesive.

Comparative Example 25

The bag-shaped structure was manufactured by the same method as in Comparative Example 25 except that the thickness of the sheet members 52 to 55 was changed from 0.13 mm to 0.75 mm.

Comparative Example 26

The bag-shaped structure was manufactured by the same method as in Comparative Example 24 except that the thickness of the sheet member 51 was changed from 0.10 mm to 0.15 mm.

Comparative Example 27

The bag-shaped structure was manufactured by the same method as in Comparative Example 24 except that the thickness of the sheet member 51 was changed from 0.10 mm to 0.15 mm and the thickness of the sheet members 52 to 55 was changed from 0.13 mm to 0.75 mm.

Comparative Example 28

The bag-shaped structure was manufactured by the same method as in Comparative Example 24 except that the thickness of the sheet member 51 was changed from 0.10 mm to 0.40 mm and the thickness of the sheet members 52 to 55 was changed from 0.13 mm to 0.30 mm.

Comparative Example 29

The bag-shaped structure was manufactured by the same method as in Comparative Example 24 except that the thickness of the sheet member 51 was changed from 0.10 mm to 0.40 mm and the thickness of the sheet members 52 to 55 was changed from 0.13 mm to 0.75 mm.

<Measurement and Evaluation>

With respect to the bag-shaped structures obtained by the methods described above, blood-vessel pressing characteristics and abnormal inflation were evaluated.

(Evaluation of Blood-Vessel Pressing Characteristics)

Blood pressure values were measured by using the aforementioned bag-shaped structures 32 in cuffs of wrist blood pressure monitors. Then, the measurement accuracy was examined. Specifically, for the wrist blood pressure monitors in which these bag-shaped structures 32 were used in the cuffs, blood pressure values were measured by alternately using the wrist blood pressure monitor and a commercially available upper-arm blood pressure monitor (Model HEM-7120 manufactured by Omron Healthcare Co., Ltd.). A blood pressure value was measured 10 times in total for each of the blood pressure monitors. Thereafter, the standard deviation was calculated with respect to differences between blood pressure values obtained by the upper-arm blood pressure monitor and blood pressure values obtained by the wrist blood pressure monitor.

With respect to blood pressure values measured by the upper-arm blood pressure monitor 10 times, the standard deviation was calculated to be about 7 mmHg. This standard deviation was set as a reference value. Accordingly, with respect to differences between blood pressure values obtained by the upper-arm blood pressure monitor and blood pressure values obtained by a wrist blood pressure monitor, when the standard deviation of these differences was below 7 mmHg, it was determined that the bag-shaped structure 32 of this wrist blood pressure monitor had excellent blood-vessel pressing characteristics, that is, this wrist blood pressure monitor realized the measurement accuracy equivalent to that of the upper-arm blood pressure monitor. On the other hand, when the standard deviation was 7 mmHg or larger, it was determined that a corresponding bag-shaped structure 32 had insufficient blood-vessel pressing characteristics, that is, a corresponding wrist blood pressure monitor did not realize the measurement accuracy equivalent to that of the upper-arm blood pressure monitor.

(Evaluation of Abnormal Inflation)

Using the bag-shaped structures 32, cuffs were manufactured, and each of the cuffs was fitted on a wrist.

In this state, each of the bag-shaped structures 32 was inflated by supplying compressed air thereto. The pressure of compressed air was 300 mmHg (=300×101325/760 Pa). The presence or absence of abnormal inflation was visually confirmed. This test was repeated three times, and the bag-shaped structure which did not cause abnormal inflation even once was evaluated as "0", whereas the bag-shaped structure which caused abnormal inflation once or more was evaluated as "x".

Table 1 shows the evaluation results of blood-vessel pressing characteristics and abnormal inflation obtained with respect to the bag-shaped structures according to Examples 1 to 17. Table 2 shows the evaluation results of blood-vessel pressing characteristics and abnormal inflation obtained with respect to the bag-shaped structures according to Examples 18 to 25.

TABLE 1

| | Sheet thickness | | | | | Standard |
| | Ta (mm) | Tc (mm) | Tc/Ta | Shore A hardness | Abnormal inflation | deviation (mmHg) |
|---|---|---|---|---|---|---|
| Ex. 1 | 0.10 | 0.15 | 1.5 | 25 | ○ | 6 |
| Ex. 2 | 0.10 | 0.30 | 3.0 | 25 | ○ | 4 |
| Ex. 3 | 0.10 | 0.40 | 4.0 | 25 | ○ | 5 |
| Ex. 4 | 0.10 | 0.60 | 6.0 | 25 | ○ | 6 |

TABLE 1-continued

| | Sheet thickness | | | | | Standard |
| | Ta (mm) | Tc (mm) | Tc/Ta | Shore A hardness | Abnormal inflation | deviation (mmHg) |
|---|---|---|---|---|---|---|
| Ex. 5 | 0.15 | 0.15 | 1.0 | 25 | ○ | 4 |
| Ex. 6 | 0.15 | 0.30 | 2.0 | 25 | ○ | 2 |
| Ex. 7 | 0.15 | 0.40 | 2.7 | 25 | ○ | 5 |
| Ex. 8 | 0.15 | 0.60 | 4.0 | 25 | ○ | 6 |
| Ex. 9 | 0.20 | 0.30 | 1.5 | 25 | ○ | 5 |
| Ex. 10 | 0.20 | 0.40 | 2.0 | 25 | ○ | 6 |
| Ex. 11 | 0.20 | 0.60 | 3.0 | 25 | ○ | 6 |
| Ex. 12 | 0.40 | 0.40 | 1.0 | 25 | ○ | 6 |
| Ex. 13 | 0.40 | 0.60 | 1.5 | 25 | ○ | 6 |
| Ex. 14 | 0.15 | 0.30 | 2.0 | 15 | ○ | 6 |
| Ex. 15 | 0.15 | 0.30 | 2.0 | 75 | ○ | 6 |
| Ex. 16 | 0.20 | 0.40 | 2.0 | 15 | ○ | 5 |
| Ex. 17 | 0.20 | 0.40 | 2.0 | 75 | ○ | 6 |

Note)
Sheet is made of silicone resin.

TABLE 2

| | Sheer thickness | | | | | Standard |
| | Ta (mm) | Tc (mm) | Tc/Ta | Shore A hardness | Abnormal inflation | deviation (mmHg) |
|---|---|---|---|---|---|---|
| Ex. 18 | 0.10 | 0.15 | 1.5 | 75 | ○ | 4 |
| Ex. 19 | 0.10 | 0.30 | 3.0 | 75 | ○ | 4 |
| Ex. 20 | 0.10 | 0.60 | 6.0 | 75 | ○ | 5 |
| Ex. 21 | 0.15 | 0.15 | 1.0 | 75 | ○ | 3 |
| Ex. 22 | 0.15 | 0.30 | 2.0 | 75 | ○ | 3 |
| Ex. 23 | 0.15 | 0.60 | 4.0 | 75 | ○ | 5 |
| Ex. 24 | 0.40 | 0.40 | 1.0 | 75 | ○ | 6 |
| Ex. 25 | 0.40 | 0.60 | 1.5 | 75 | ○ | 6 |

Note)
Sheet is made of TPU resin.

As shown in Tables 1 and 2, the bag-shaped structure caused no abnormal inflation and the standard deviation was decreased in the case of using the bag-shaped structures according to Examples 1 to 25. Especially in the case of using the bag-shaped structures according to Examples 2, 5, 6, 18, 19, 21, and 22, the standard deviation was further decreased.

Table 3 shows the evaluation results of blood-vessel pressing characteristics and abnormal inflation obtained with respect to the bag-shaped structures according to Comparison Examples 1 to 23. Table 4 shows the evaluation results of blood-vessel pressing characteristics and abnormal inflation obtained with respect to the bag-shaped structures according to Comparison Examples 24 to 29.

TABLE 3

| | Sheet thickness | | | | | Standard |
| | Ta (mm) | Tc (mm) | Tc/Ta | Shore A hardness | Abnormal inflation | deviation (mmHg) |
|---|---|---|---|---|---|---|
| Comp. Ex. 1 | 0.10 | 0.13 | 1.3 | 25 | x | 10 |
| Comp. Ex. 2 | 0.10 | 0.75 | 7.5 | 25 | ○ | 10 |
| Comp. Ex. 3 | 0.15 | 0.13 | 0.9 | 25 | x | 9 |
| Comp. Ex. 4 | 0.15 | 0.75 | 5.0 | 25 | ○ | 9 |
| Comp. Ex. 5 | 0.20 | 0.13 | 0.7 | 25 | x | 21 |
| Comp. Ex. 6 | 0.20 | 0.15 | 0.8 | 25 | ○ | 9 |
| Comp. Ex. 6 | 0.20 | 0.15 | 0.8 | 25 | ○ | 9 |
| Comp. Ex. 7 | 0.20 | 0.75 | 3.8 | 25 | ○ | 12 |
| Comp. Ex. 8 | 0.40 | 0.13 | 0.3 | 25 | x | 36 |
| Comp. Ex. 9 | 0.40 | 0.15 | 0.4 | 25 | ○ | 21 |
| Comp. Ex. 10 | 0.40 | 0.30 | 0.8 | 25 | ○ | 14 |
| Comp. Ex. 11 | 0.40 | 0.75 | 1.9 | 25 | ○ | 15 |

TABLE 3-continued

|  | Sheet thickness | | | Shore A hardness | Abnormal inflation | Standard deviation (mmHg) |
| --- | --- | --- | --- | --- | --- | --- |
|  | Ta (mm) | Tc (mm) | Tc/Ta |  |  |  |
| Comp. Ex. 12 | 0.05 | 0.15 | 3.0 | 25 | ○ | 15 |
| Comp. Ex. 13 | 0.50 | 0.15 | 0.3 | 25 | ○ | 29 |
| Comp. Ex. 14 | 0.05 | 0.30 | 6.0 | 25 | ○ | 13 |
| Comp. Ex. 15 | 0.50 | 0.30 | 0.6 | 25 | ○ | 22 |
| Comp. Ex. 16 | 0.05 | 0.40 | 8.0 | 25 | ○ | 19 |
| Comp. Ex. 17 | 0.50 | 0.40 | 0.8 | 25 | ○ | 18 |
| Comp. Ex. 18 | 0.05 | 0.60 | 12.0 | 25 | ○ | 8 |
| Comp. Ex. 19 | 0.50 | 0.60 | 1.2 | 25 | ○ | 19 |
| Comp. Ex. 20 | 0.15 | 0.30 | 2.0 | 10 | ○ | 8 |
| Comp. Ex. 21 | 0.15 | 0.30 | 2.0 | 90 | ○ | 8 |
| Comp. Ex. 22 | 0.20 | 0.40 | 2.0 | 10 | x | 8 |
| Comp. Ex. 23 | 0.20 | 0.40 | 2.0 | 90 | ○ | 9 |

Note)
Sheet is made of silicone resin.

TABLE 4

|  | Sheet thickness | | | Shore A hardness | Abnormal inflation | Standard deviation (mmHg) |
| --- | --- | --- | --- | --- | --- | --- |
|  | Ta (mm) | Tc (mm) | Tc/Ta |  |  |  |
| Comp. Ex. 24 | 0.10 | 0.13 | 1.3 | 75 | x | 13 |
| Comp. Ex. 25 | 0.10 | 0.75 | 7.5 | 75 | ○ | 14 |
| Comp. Ex. 26 | 0.15 | 0.13 | 0.9 | 75 | x | 18 |
| Comp. Ex. 27 | 0.15 | 0.75 | 5.0 | 75 | ○ | 20 |
| Comp. Ex. 28 | 0.40 | 0.30 | 0.8 | 75 | x | 18 |
| Comp. Ex. 29 | 0.40 | 0.75 | 1.9 | 75 | ○ | 25 |

Note)
Sheet is made of TPU resin.

As shown in Tables 3 and 4, in the case of using the bag-shaped structures according to Comparative Examples 1, 3, 5, 8, 22, 24, 26, and 28, the abnormal inflation occurred and the standard deviation reached 7 mmHg or more. In the case of using the bag-shaped structures according to the rest of comparative examples, no abnormal inflation occurred; however, the standard deviation reached 7 mmHg or more.

The invention claimed is:

1. A bag-shaped structure for use in a cuff for a blood pressure monitor that is configured to be wrapped around a living body and is inflated by supplying a fluid to an internal space to apply a pressure to the living body, comprising:
an inner wall portion that is made of a thermoset elastomer and configured to be provided on the living body's side, has a Shore A hardness within a range of 20 to 30, and has a thickness within a range of 0.12 mm to 0.18 mm;
an outer wall portion that faces the inner wall portion; and
a pair of side wall portions that are provided in a manner to be continuous with the inner wall portion and the outer wall portion, have a Shore A hardness equal to the Shore A hardness of the inner wall portion, and have a thickness that falls within a range of 0.25 mm to 0.35 mm.

2. The bag-shaped structure according to claim 1, wherein each of the side wall portions forming the pair is bent or folded toward the internal space.

3. The bag-shaped structure according to claim 1, wherein each of the side wall portions forming the pair has a plurality of regions bent or folded toward the internal space.

4. The bag-shaped structure according to claim 1, further comprising a coupling portion between the inner wall portion and the outer wall portion, wherein the coupling portion includes a sheet provided with one or more communication holes, couples the pair of side wall portions together, divides the internal space into a first internal space and a second internal space, and allows communication between the first internal space and the second internal space through the one or more communication holes.

5. The bag-shaped structure according to claim 1, having a width within a range of 20 mm to 45 mm.

6. A cuff for a blood pressure monitor, comprising the bag-shaped structure according to claim 1.

7. A blood pressure monitor comprising the cuff according to claim 6.

* * * * *